United States Patent
Marashdeh et al.

(10) Patent No.: US 10,551,339 B2
(45) Date of Patent: *Feb. 4, 2020

(54) SMART CAPACITANCE SENSORS FOR USE WITH ELECTRICAL CAPACITANCE VOLUME TOMOGRAPHY AND CAPACITANCE SENSING APPLICATIONS

(71) Applicant: TECH4IMAGING LLC, Columbus, OH (US)

(72) Inventors: Qussai Marashdeh, Columbus, OH (US); Yousef Alghothani, Columbus, OH (US); Christopher Zuccarelli, Columbus, OH (US)

(73) Assignee: Tech4Imaging LLC, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/937,050

(22) Filed: Mar. 27, 2018

(65) Prior Publication Data

US 2018/0224388 A1    Aug. 9, 2018

Related U.S. Application Data

(63) Continuation of application No. 15/152,031, filed on May 11, 2016, now Pat. No. 9,958,408.

(51) Int. Cl.
*G01R 27/26* (2006.01)
*G01R 27/22* (2006.01)
(Continued)

(52) U.S. Cl.
CPC ............ *G01N 27/221* (2013.01); *A61B 5/05* (2013.01); *A61B 5/0535* (2013.01);
(Continued)

(58) Field of Classification Search
CPC .. G01N 27/221; G01N 27/226; G01N 27/228; G01N 27/2605; G01N 33/2823; G01F 1/64; G01F 1/74
See application file for complete search history.

(56) References Cited

U.S. PATENT DOCUMENTS

| | | | |
|---|---|---|---|
| 5,130,661 A | 7/1992 | Beck et al. | |
| 5,262,730 A | 11/1993 | Smith et al. | |
| (Continued) | | | |

FOREIGN PATENT DOCUMENTS

| | | |
|---|---|---|
| CN | 102954854 A | 3/2013 |
| EP | 0606115 A1 | 7/1994 |
| (Continued) | | |

OTHER PUBLICATIONS

Gunes, C. et al., A Comparison Between Electrical Capacitance Tomography and Displacement—Current Phase Tomography, IEEE Sensors Journal, Dec. 15, 2017, vol. 17, No. 24.
(Continued)

*Primary Examiner* — Minh N Tang
(74) *Attorney, Agent, or Firm* — Standley Law Group LLP

(57) ABSTRACT

A stretchable capacitance sensor having multiple components for communicating signals to a data acquisition system for reconstructing an image of an area or object located in a subject being sensed, and for calculating the shape or conformity that it is in. The stretchable sensor consists of an inner layer of plates that provide the capacitance data, a middle layer of plates that provide the geometry-sensing data, and an outer layer of plates that serves as the shielding ground layer. The configuration of all three components can be variably changed to increase the capacitance data channels, increase or decrease flexibility and stretchability of the sensor, and increase the spatial resolution of the geometry sensing feature. The sensor is adapted to communicate
(Continued)

signals to a data acquisition system for providing an image of the area or object between the capacitance plates.

19 Claims, 12 Drawing Sheets

(51) Int. Cl.
- *G01N 27/22* (2006.01)
- *G01F 1/64* (2006.01)
- *A61B 5/053* (2006.01)
- *A61B 5/00* (2006.01)
- *A61B 5/05* (2006.01)
- *G01F 17/00* (2006.01)

(52) U.S. Cl.
CPC .......... *A61B 5/0536* (2013.01); *A61B 5/6802* (2013.01); *G01F 1/64* (2013.01); *G01N 27/226* (2013.01); *A61B 5/053* (2013.01); *A61B 2562/0214* (2013.01); *A61B 2562/046* (2013.01); *G01F 17/00* (2013.01)

(56) References Cited

U.S. PATENT DOCUMENTS

| | | | |
|---|---|---|---|
| 5,279,163 | A | 1/1994 | D'Antonio et al. |
| 6,208,204 | B1 | 6/2001 | Suzuki et al. |
| 7,424,462 | B2 | 9/2008 | Avni et al. |
| 7,684,846 | B2 | 3/2010 | Johnson et al. |
| 8,461,852 | B2 | 6/2013 | Yang et al. |
| 8,508,238 | B2 | 8/2013 | Mahalingham et al. |
| 8,519,722 | B1 | 8/2013 | Prendergast |
| 8,614,707 | B2 | 12/2013 | Warsito et al. |
| 8,867,928 | B2 | 10/2014 | Piehler |
| 9,016,143 | B2 | 4/2015 | Mamigonians |
| 9,170,224 | B2 | 10/2015 | Fan et al. |
| 9,259,168 | B2 | 2/2016 | Marashdeh et al. |
| 9,579,038 | B2 | 2/2017 | Brunner et al. |
| 9,581,560 | B2 | 2/2017 | Fan et al. |
| 9,927,385 | B2 | 3/2018 | Marashdeh et al. |
| 9,958,408 | B2 * | 5/2018 | Marashdeh .......... G01N 27/221 |
| 2002/0028010 | A1 | 3/2002 | Toida |
| 2003/0020493 | A1 | 1/2003 | Haase et al. |
| 2003/0173958 | A1 | 9/2003 | Goldfine et al. |
| 2004/0233191 | A1 | 11/2004 | Mukherjee et al. |
| 2005/0167588 | A1 | 8/2005 | Donnangelo |
| 2007/0024278 | A1 | 2/2007 | Walters et al. |
| 2007/0133746 | A1 | 6/2007 | Ortiz Aleman et al. |
| 2008/0116995 | A1 | 5/2008 | Kim et al. |
| 2009/0272028 | A1 | 11/2009 | Drozd et al. |
| 2010/0132473 | A1 | 6/2010 | Willcox |
| 2010/0148804 | A1 | 6/2010 | Jakoby et al. |
| 2010/0332170 | A1 | 12/2010 | Gao et al. |
| 2011/0109911 | A1 | 5/2011 | Podoleanu |
| 2012/0268135 | A1 | 10/2012 | Marsala et al. |
| 2013/0187641 | A1 | 7/2013 | Singer |
| 2013/0275082 | A1 | 10/2013 | Follmer et al. |
| 2013/0327154 | A1 | 12/2013 | Xie et al. |
| 2014/0361793 | A1 | 12/2014 | Marashdeh et al. |
| 2014/0365009 | A1 | 12/2014 | Wettels |
| 2014/0365152 | A1 | 12/2014 | Marashdeh et al. |
| 2015/0048852 | A1 | 2/2015 | Marshdeh et al. |
| 2015/0338364 | A1 | 11/2015 | Fan et al. |
| 2016/0025663 | A1 | 1/2016 | Lehikoinen et al. |
| 2016/0076926 | A1 | 3/2016 | McCann et al. |
| 2016/0091448 | A1 | 3/2016 | Soleimani |
| 2016/0206227 | A1 | 7/2016 | Marashdeh et al. |
| 2016/0310040 | A1 | 10/2016 | Marashdeh |
| 2016/0327503 | A1 | 11/2016 | Marashdeh et al. |
| 2017/0241817 | A1 | 8/2017 | Marashdeh et al. |

FOREIGN PATENT DOCUMENTS

| | | |
|---|---|---|
| WO | 2010007096 A1 | 1/2010 |
| WO | 2011002793 A1 | 1/2011 |

OTHER PUBLICATIONS

Wang, F. et al., Electrical Capacitance Volume Tomography: Design and Applications, Sensors, 2010 pp. 1890-1917.

Wikipedia, Electrical Capacitance Volume Tomography, https://en.wikipedia.org/w/index.php?title=Electrical_capacitance_volume_tomography&oldid=868112998, site visited Dec. 7, 2018.

Huang et al., Design of Sensor Electronics for Electrical Capacitance Tomography, IEE Proceedings G (Circuits, Devices and Systems), vol. 139, Issue 1, Feb. 1992, p. 83-88.

Marashdeh, Q. et al., Adaptive Electrical Capacitance Volume Tomography, IEEE Sensors Journal, Apr. 2014, pp. 1253-1259, vol. 14, No. 4.

Yang, W. et al., Image Reconstruction Algorithms for Electrical Capacitance Tomography, Measurement Science and Technology 14, 2003, pp. R1-R13.

Xie, C. et al., Electrical Capacitance Tomography for Flow Imaging: System Model for Development of Image Reconstruction Algorithms and Design of Primary Sensors, IEEE Proceedings—G, Feb. 1992, pp. 89-98, vol. 139, No. 1.

Chew, W. et al., Reconstruction of Two-Dimensional Permittivity Distribution Using the Distorted Born Iterative Method, IEEE Transactions on Medical Imaging, Jun. 1990, pp. 218-225, vol. 9, No. 2.

Marashdeh, et al., "On the ECT Sensor Based Dual Imaging Modality System for Electrical Permittivity and Conductivity Measurements", 2006, pp. 1-6, The Ohio State University, Columbus, Ohio.

Warsito, et al., "Electrical Capacitance Volume Tomography", 2007, pp. 1-9.

Covilakam, M., "Evaluation of Structural Monitoring Methods for Large Diameter Water Transmission Pipelines", Dec. 2011, The University of Texas at Arlington.

* cited by examiner

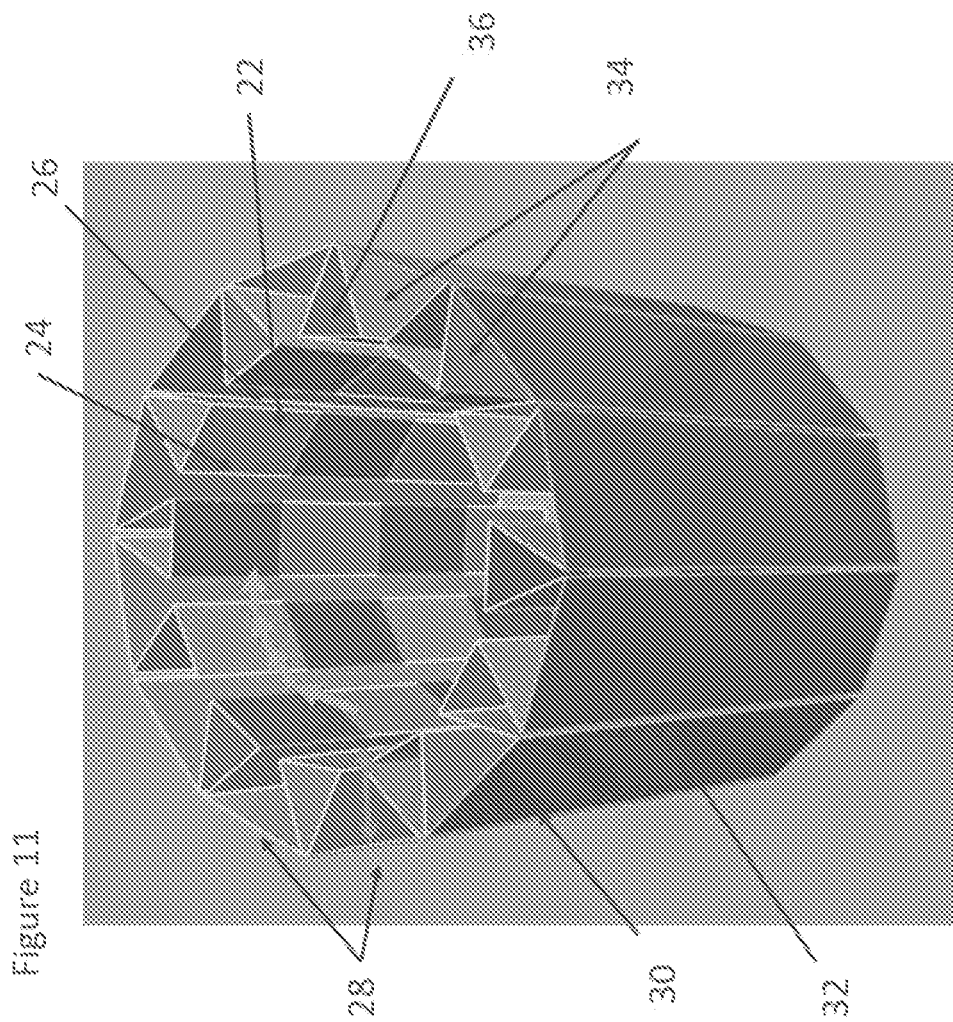

SMART CAPACITANCE SENSORS FOR USE WITH ELECTRICAL CAPACITANCE VOLUME TOMOGRAPHY AND CAPACITANCE SENSING APPLICATIONS

CROSS-REFERENCE TO RELATED APPLICATIONS

This is a continuation of U.S. Pat. No. 9,958,408, filed May 11, 2016, the content of which is incorporated herein by reference.

BACKGROUND OF THE INVENTIVE FIELD

Electrical Capacitance Volume Tomography (ECVT) is a non-invasive imaging modality. Its applications span an array of industries. Most notably, ECVT is applicable to multiphase flow applications commonly employed in many industrial processes. ECVT is often the technology of choice due to its advantages of high imaging speed, scalability to different process vessels, flexibility, and safety. In ECVT, sensor plates are distributed around the circumference of the column, object or vessel under interrogation. The number of sensor plates may be increased to acquire more capacitance data. However, increasing the number of sensor plates reduces the area of each sensor plate accordingly. A limit exists on the minimum area of a sensor plate for a given column diameter, thus limiting the maximum number of plates that can be used in an ECVT sensor. This limit is dictated by the minimum signal-to-noise ratio requirement of the data acquisition system. Since ECVT technology is based on recording changes in capacitance measurements induced by changes in dielectric distribution (i.e., phase distribution), and the capacitance level of a particular sensor plate combination is directly proportional to the area of the plates, minimum signal levels are needed to provide sufficiently accurate measurements. These considerations dictate the required minimum sensor plate dimensions. This limitation on the minimum size of the sensor plates, while increasing the number of available sensor plates in an ECVT sensor, is one of the main hurdles in achieving a high resolution imaging system.

To overcome this challenge, the concept of Adaptive Electrical Capacitance Volume Tomography (AECVT) was recently developed, whereby the number of independent capacitance measurements is increased through the use of reconfigurable synthetic sensor plates composed of many smaller sensor plates (constitutive segments). These synthetic sensor plates maintain the minimum area for a given signal-to-noise ratio (SNR) and acquisition speed requirements while allowing for many different combinations of (synthetic) sensor plates in forming a sensor plate pair.

Electrical Capacitance Tomography (ECT) is the reconstruction of material concentrations of dielectric physical properties in the imaging domain by inversion of capacitance data from a capacitance sensor. Electrical Capacitance Volume Tomography or ECVT is the direct 3D reconstruction of volume concentrations or physical properties in the imaging domain utilizing 3D features in the ECVT sensor design. ECVT technology is described in U.S. Pat. No. 8,614,707 to Warsito et al. which is hereby incorporated by reference.

Adaptive Electrical Capacitance Volume Tomography (AECVT) provides higher resolution volume imaging of capacitance sensors based on different levels of activation levels on sensor plate segments. AECVT is described in U.S. Patent Application Publication US2013/0085365 A1 to Marashdeh et al. which is hereby incorporated by reference.

In ECT, ECVT, or AECVT, the capacitance measurement between sensor plates is also related to the effective dielectric content between that plate pair. The SART method can be extended to all measurements of ECT, ECVT, or AECVT sensors, thus providing a high resolution visual representation of each phase through image reconstruction.

Electrical capacitance sensors are used for non-invasive imaging by distributing the electric field inside the imaging domain in 3D. ECVT sensors enable sensitivity variation in the imaging domain that can utilize different plate shapes and distributions to target a volume for imaging. They exhibit flexibility for fitting around different sizes and geometries and are scalable to different sizes. Capacitance sensors so far have been focused on being passively applied around a geometry. In such arrangements, the capacitance plates are designed to fit around the targeted geometry and the sensor shape is recorded for image reconstruction purposes. In the present invention, capacitance sensors are designed with a smart feature that enables the sensor to detect and quantify the geometry it is placed around. Capacitance sensors in this case are developed from flexible materials that can be used for imaging volumes of different shapes or sizes. The smart capacitance sensor is able to detect the shape and size of the volume it is placed around formulate a sensitivity matrix for such volume, acquire capacitance measurements, and provide reconstructed images. Each pair of inner geometry sensor plates detect a capacitance signal that has information on how much the sensor stretched in that region. The difference in stretch-ability around the geometry is used to infer the shape of the geometry. The total stretch of the sensor tells the volumes. For example, in FIG. 5b, you can see the sensor stretching more where the geometry is larger. The geometry plates would be able to detect this difference and infer a shape.

The present invention also relates to stretchable, flexible, wearable, and modular capacitance sensors for applications that involve tomography imaging. In prior technologies (patent application Ser. No. 13/965,636), stretchable, flexible, wearable, and modular capacitance sensors are designed based on 2D stretching of the sensor area. In the present invention, the stretching is based on shrinking or expanding a third (depth) dimension that is also equipped with capacitance or other sensors to detect and quantify the distance of sensor plates from each other. This feature enables the sensor to measure and quantify the shape and size of the volume it is placed around. The inner folded regions have plates on the surfaces. When the sensor stretches, the distance between those plates grows larger and the capacitance between them becomes less. Thus, the measured capacitance between those inner plates is used to measure stretch-ability in the locality of those inner plates. Different stretch-ability measurements around the object is used to infer a geometry from which a volume is also calculated.

In the present invention, curved plates are also allowed to reduce hot spots of sensitivity in the imaging domain. Those hot spots complicate the image reconstruction process.

SUMMARY OF THE GENERAL INVENTIVE CONCEPT

The present invention is directed to electrical capacitance sensing and process tomography and, in particular, to Electrical Capacitance Volume Tomography (ECVT) and adaptive ECVT sensors and using design techniques for 3D realizing flexible, wearable, stretchable, and modular ECVT sensors.

Dynamic ECVT is a technology that senses measured capacitances between sensor plates to generate a whole volume image of the region. ECVT technology has been applied in providing images of objects moving through a pipe for example. ECVT has provided insight into multi-phase flow phenomena in many industrial processes, including pneumatic conveying, oil pipe lines, fluidized beds, bubble columns and many other chemical and biochemical processes (the multiphase flow often being in a combination of gas, liquid, and solid states). ECVT may also be used for imaging biological processes and tissues or other static or stationery objects.

Capacitance sensing sensors were designed previously to address fixed structure applications surrounding a dynamic flow component or a static structure. The design of the present invention includes the integration of all plates, connectors, resistors, and shielding layers into one flexible or stretchable element. The present invention provides an innovative design with features through which the sensor can be used repeatedly and on different subjects (columns, pipes, organs, or limbs, etc.) through relatively simple installations. Specifically, features of the preferred embodiment of the present invention includes the integration of all components of a capacitance sensor into one element that is stretchable and conformable to different geometries by stretching or compressing the depth dimension of the sensor. This will allow one sensor to be used in a variety of different applications, for example a variety of pipe diameters and shapes, or a wearable feature where sensors can be placed by users at different parts of the human body, or inspection tasks where the object is stationary. Details of these features are described below.

The integrative design of the present invention combines all elements of a capacitance sensor into one 3D flexible and stretchable design that can be used repeatedly. This design in the preferred embodiment contains three layers including the inner layers of capacitance plates, the outer layer of ground shielding plates, and an intermediate layer that connects the two and also includes the geometry-sensing plates. Low profile connectors preferably connect the plates to coaxial cables. The plate layer contains a design of capacitance sensors aimed at distributing the electric field in three dimensions. Traces can be separated from each other by distance to reduce capacitive coupling. The shielding ground layer preferably provides isolation for the capacitance sensors from outside capacitance coupling or electric noise. In one embodiment, the low profile connectors directly connect the sensor plates to data acquisition system through coaxial cables. The integrative design here enables capacitance sensors to be used easily for wrapping around different geometries. It also provides a means for a wearable feature where sensors can be placed on the human body in a low profile manner. It also provides a stretchable sensor where sensor elements can be extended for applications where object intended for imaging may change in size or geometry. This integrative approach can be applied for ECVT sensors of different designs and varying number of plates.

The integrative design of the present invention also preferably includes a modular feature where plates fabricated in an integrative approach can be layered separately for forming an equivalent plate. Such feature enables changing sensor design using modular sensors/plates.

The present invention also includes a stretchable feature where sensor plates and layers are fabricated onto a stretchable substrate. For example, stretchable materials can be a formed of flexible boards that flex in more than one dimension or flexible metal meshes used for fabricating conductive layers. The flexibility can also be provided by connecting flexible integrative sensor sections using stretchable connections. Flexibility can also be provided using conductive spray on stretchable isolative materials (like rubber or elastic material or even stretchable fabric) to form layers of integrative sensors as explained above.

The interactive design of the present invention also includes a geometry sensing feature that can automatically sense the configuration and geometry the sensor is in. The geometry sensing plates are located in the intermediate triangular layer that connects the inside and outside layer and allows the sensor to flex in the second or third dimension, thus expanding. The geometry sensing plates will also be able to detect any immediate or real-time changes in configuration and geometry of the sensor. When the capacitance of the geometry sensing plates is being logged continuously, any change in geometry can immediately be detected. The signal is preferably sent via coaxial cable to the data-acquisition box which can account for the changes in reproducing the three dimensional capacitance image of the sensor. The signal is then analyzed to detect changes in sensor size or geometry and formulate required sensitivity matrix for imaging of such geometry.

The integrative design of the present invention also allows 3D formations of sensing plates to better control sensitivity of sensor in the imaging domain. In the preferred embodiment, the sensor plate is convex to direct a more uniform sensitivity into the imaging domain.

Traditional sensor plates used in Electrical Capacitance Volume Tomography (ECVT) are flat or follow the contour of the sensing region. The array of sensor plates also traditionally occupies as much of the sensing region's surface area as possible. This configuration causes adjacent plates to have an undesired, high-value fringing effect on the plate edges closest to one another. This can negatively affect physical measurements, as well as the quality of images reconstructed from ECVT.

Images are reconstructed from a sensitivity matrix that relates sensor capacitance to dielectric distribution in a 3D space. This sensitivity matrix is usually built with simulation software. With a traditional plate design having flat, tightly-packed plates, there is a high electric field near adjacent plate edges. This effect is carried into generated 3D images, causing undesired shadows to appear at these spots between plates.

To combat this effect, sensor plates are placed as convex surfaces, with their edges curving away from the sensing region. Doing so reduces the fringing effect seen in images by bringing the fringe area away from the region to be imaged, and reducing the strength of the fringe electric field overall. Plates are built as convex shapes, with edges curving away from the sensing region, to ensure their fringe effects will not affect the measurements of the sensing region.

The integrative design of the present invention also enables measuring of capacitance signals from an Adaptive Electrical Capacitance Volume Tomography (AECVT) sensor.

In one embodiment of the invention, the stretchable sensor apparatus is comprised of a substrate comprising: a plurality of inner portions arranged in a circular arrangement, each inner portion having a first and second side, a plurality of outer portions arranged in a circular arrangement, each outer portion having a first and second side, a plurality of intermediate portions, each intermediate portion connecting a side of one of the outer portions with a side of one of the inner portions and wherein the substrate is adapted to be stretched around objects of various diameters and shapes; a plurality of capacitance plates, each of the capacitance plates attached to one of the plurality of inner portions; a plurality of shielding ground plates, each of the shielding ground plates attached to one of the plurality of outer portions; a plurality of geometry sensing plates, each of the geometry sensing plates attached to one of the plurality of intermediate portions. The plurality of geometry sensing plates are adapted to detect signals for determining the shape of the volume the sensor is placed around. The ends of the intermediate portions and inner portions form triangle shapes when then sensor is in the closed, non-stretched position.

In one embodiment, the capacitance plates are arranged in a staggered arrangement around the plurality of inner portions of the substrate. The geometry sensing plates are preferably capacitance plates adapted to sense the capacitance between the capacitance plates. The sensor is adapted to sense capacitance between the geometry sensing plates for determining the amount of compression or expansion of the sensor. In other words, as the length of the distance between the capacitance plates increases the capacitance decreases. This change in capacitance can be used to determine the distance between the plates and the geometry of the object or area the sensor is placed around.

The foregoing and other features and advantages of the present invention will be apparent from the following more detailed description of the particular embodiments, as illustrated in the accompanying drawings.

BRIEF DESCRIPTION OF THE DRAWINGS

The following detailed description of the example embodiments refers to the accompanying figures that form a part thereof. The detailed description provides explanations by way of exemplary embodiments. It is to be understood that other embodiments may be used having mechanical and electrical changes that incorporate the scope of the present invention without departing from the spirit of the invention.

In addition to the features mentioned above, other aspects of the present invention will be readily apparent from the following descriptions of the drawings and exemplary embodiments, wherein like reference numerals across the several views refer to identical or equivalent features, and wherein:

A better understanding of an exemplary embodiment will be obtained from a reading of the following detailed description and the accompanying drawings wherein identical reference characters refer to identical parts and in which:

FIG. 1A illustrates one embodiment of a stretchable sensor design of the present invention.

FIG. 1B illustrates a top view of the sensor in FIG. 1A.

FIG. 2A illustrates the sensor in FIG. 1 in a stretched embodiment.

FIG. 2B illustrates a top view of the sensor of FIG. 2A.

FIG. 3A illustrates a top view of one embodiment of a stretchable sensor in an example configuration.

FIG. 3B illustrates the side view of the sensor of FIG. 3A.

FIG. 4A illustrates a top view of the stretchable sensor of FIG. 3A in another example configuration.

FIG. 4B illustrates the side view of the sensor of FIG. 4A.

FIG. 5A illustrates a top view of the stretchable sensor of FIG. 3A in another example configuration.

FIG. 5B illustrates the side view of the sensor of FIG. 5A.

FIG. 6A illustrates the top view of the sensor in FIG. 3A configured around a complex shape.

Figure 6A:
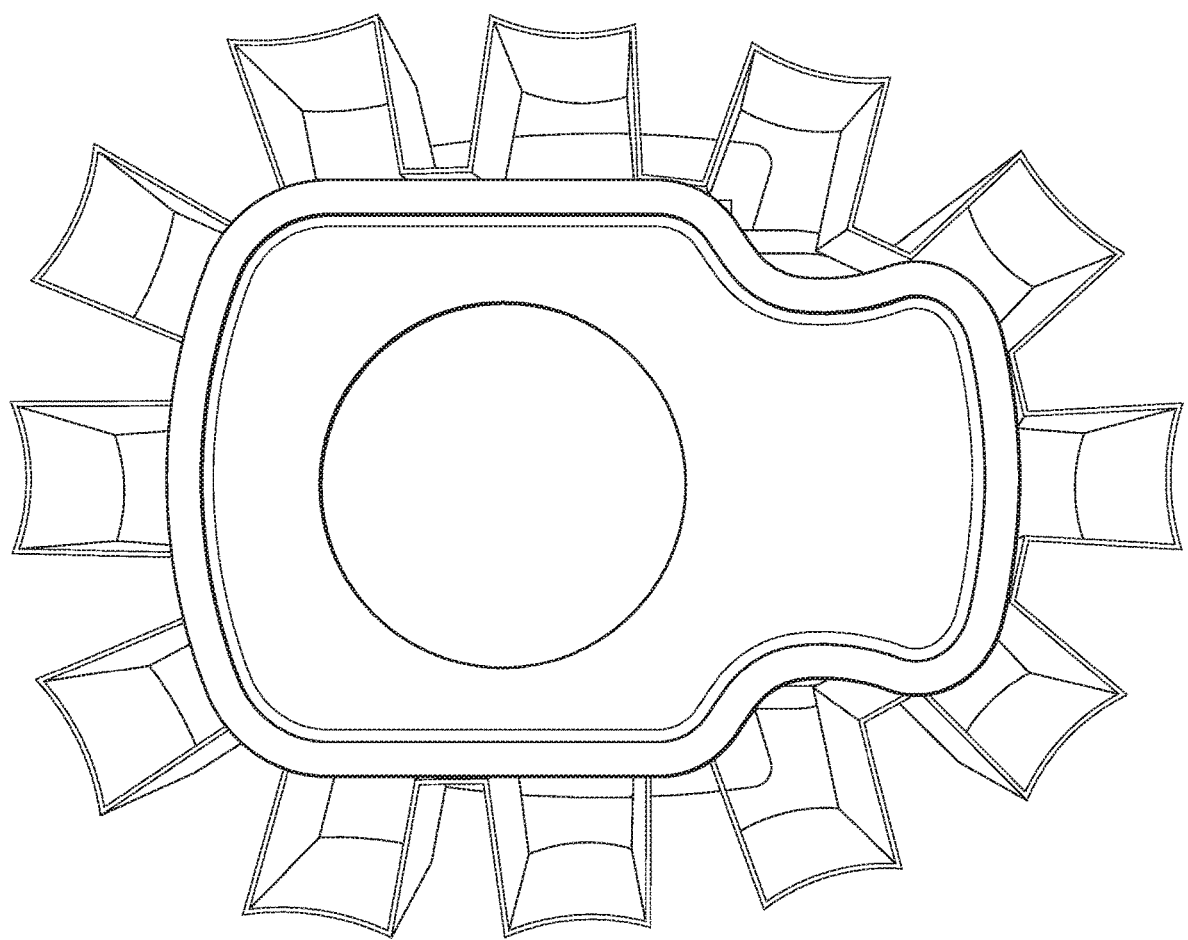
Figure 6B:
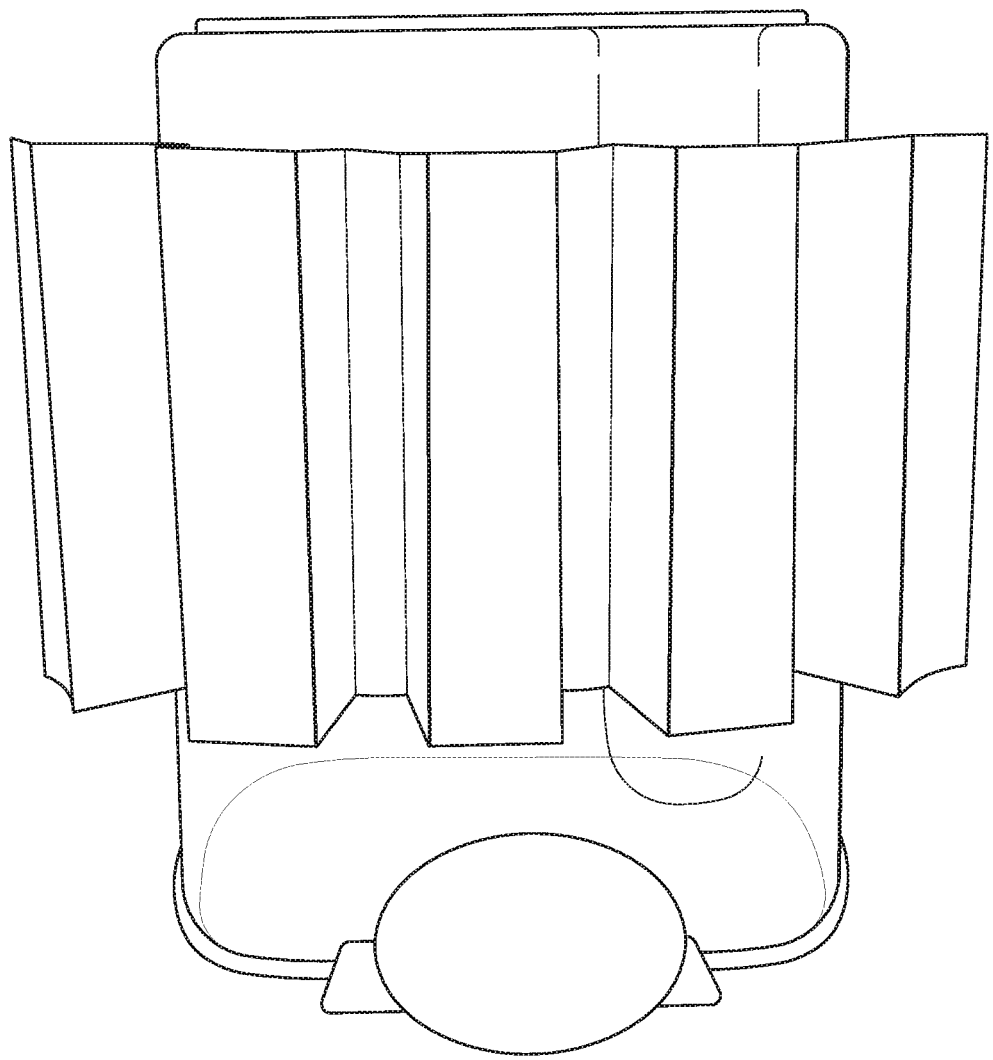

FIG. 6B illustrates FIG. 6A from the side view.

Figure 7:
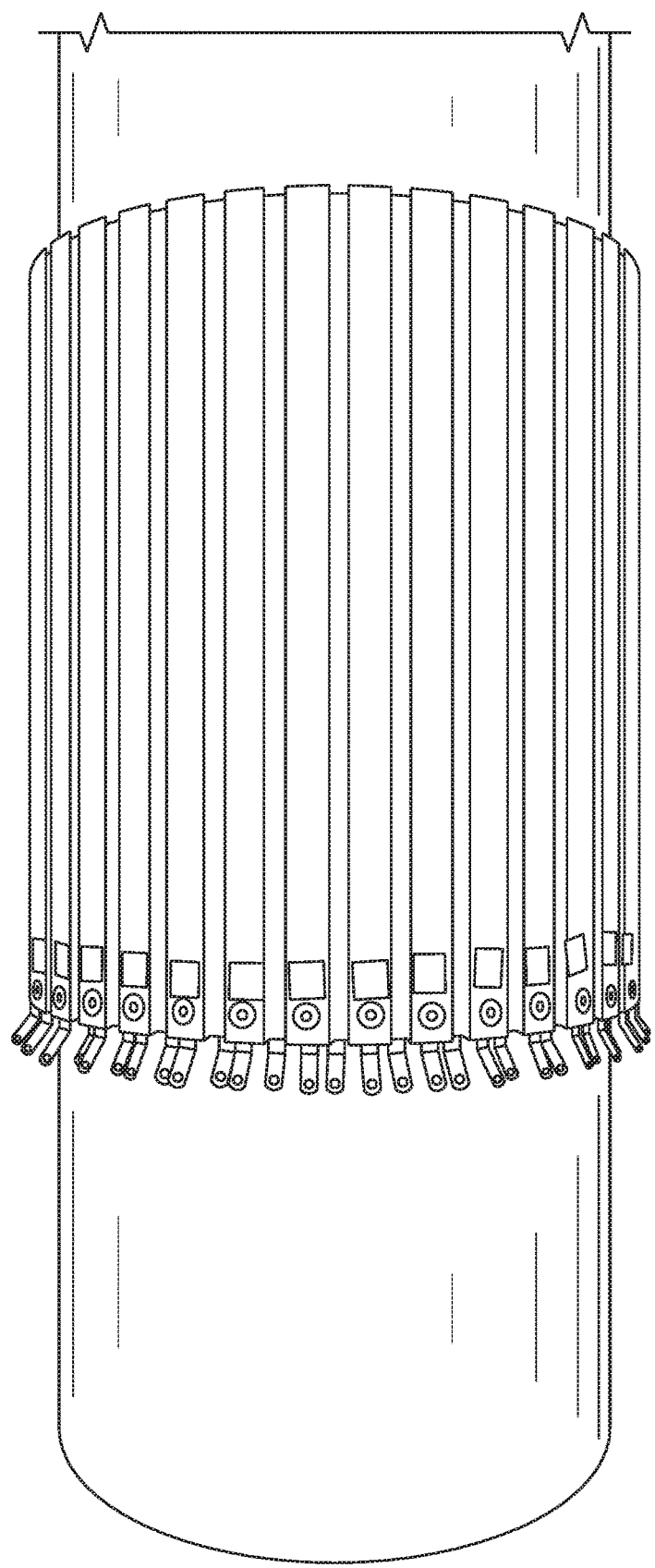

FIG. 7 illustrates a side view of one embodiment of a stretchable sensor with 36 channels.

Figure 8:
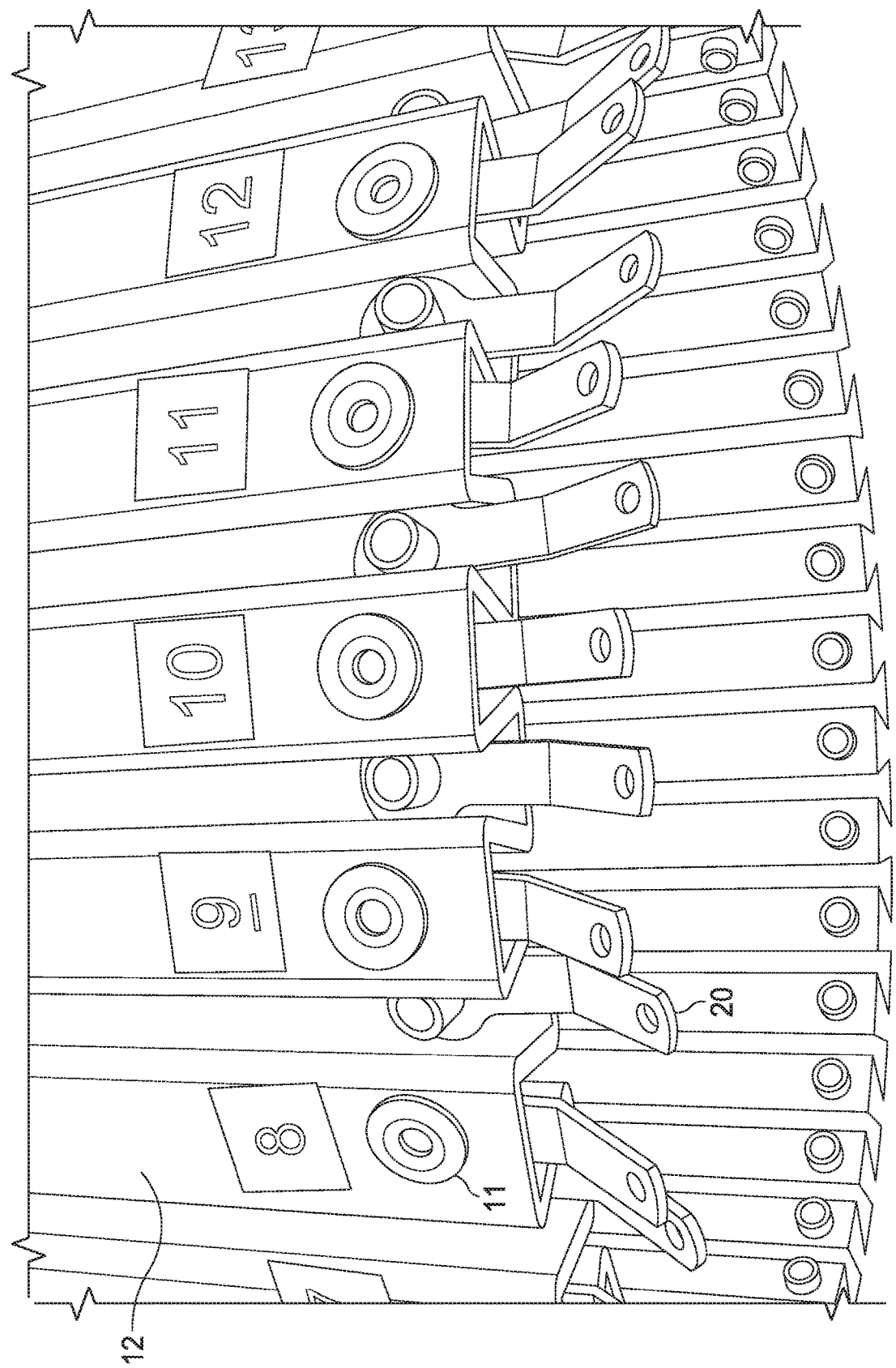

FIG. 8 illustrates one embodiment of the low profile connectors that are used to connect the capacitive, ground, and geometry-sensing plates of the stretchable sensor to the data acquisition via coaxial cables.

Figure 9:
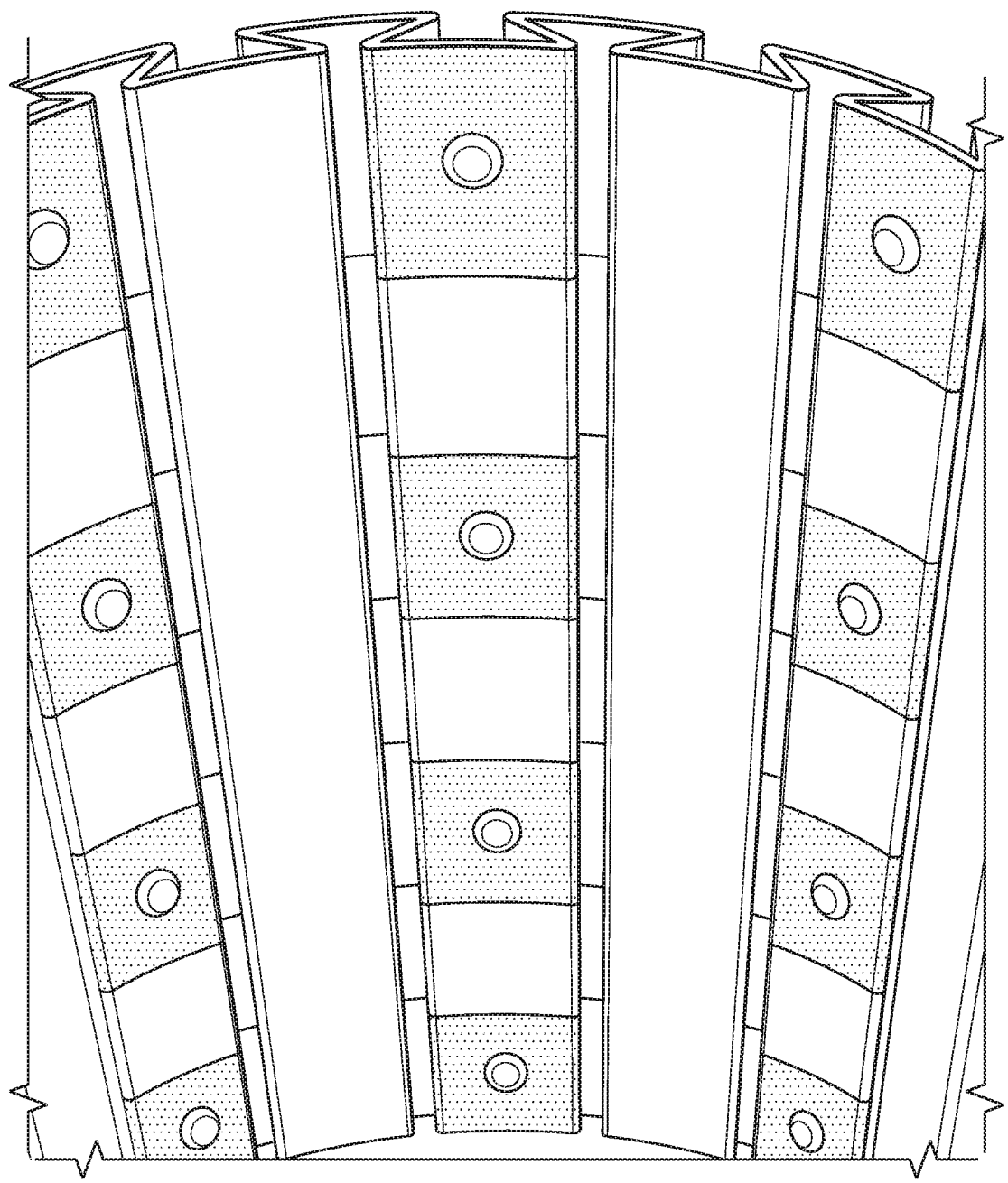

FIG. 9 illustrates one arrangement of inner sensor plate connections.

Figure 10B:
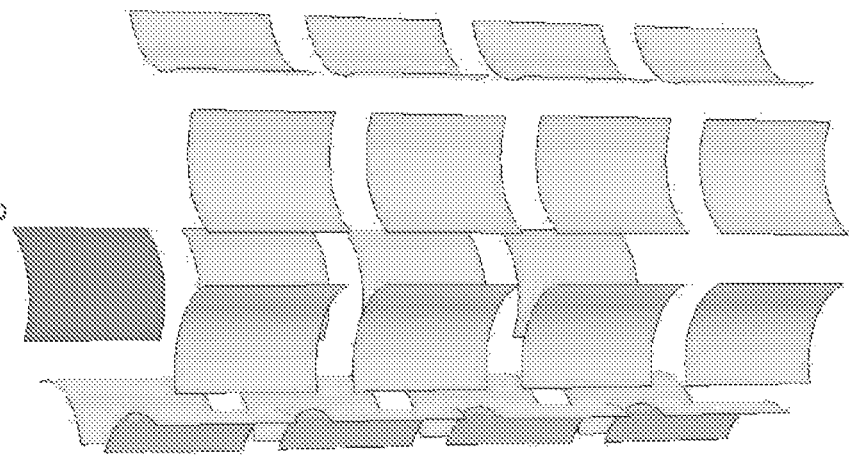
Figure 10A:
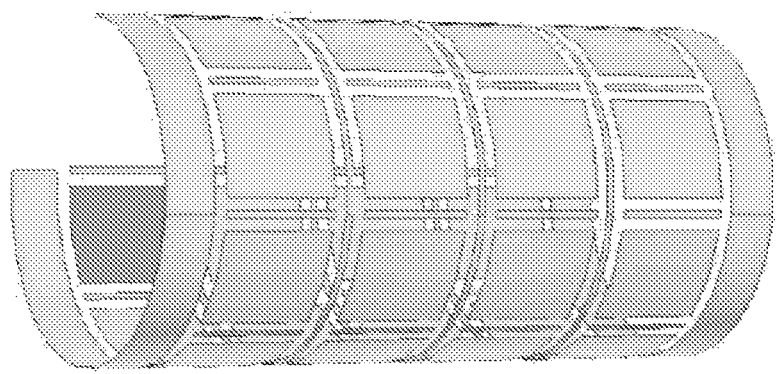

FIG. 10A illustrates one example of conventional shaped capacitance plates.

FIG. 10B illustrates one example of convex shaped capacitance plates.

FIG. 11 illustrates one embodiment of the sensor of the present invention showing dimensions indicated by arrows.

DETAILED DESCRIPTION OF THE PREFERRED EMBODIMENTS

Figure 1B:
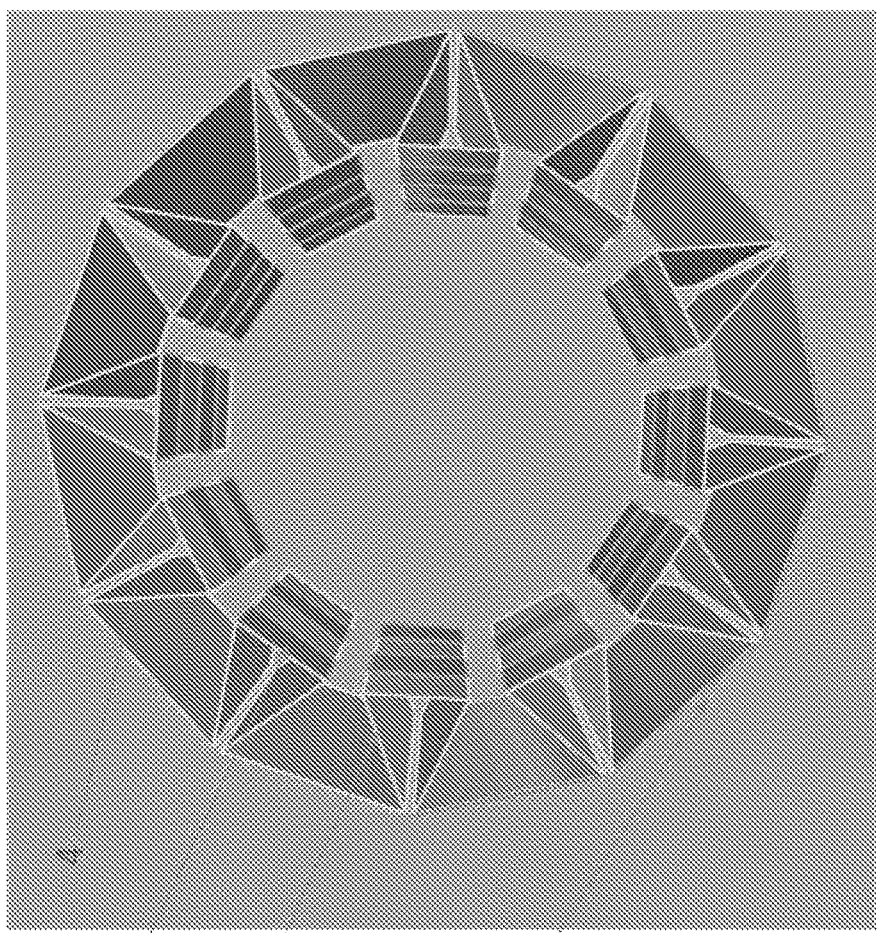
Figure 1A:
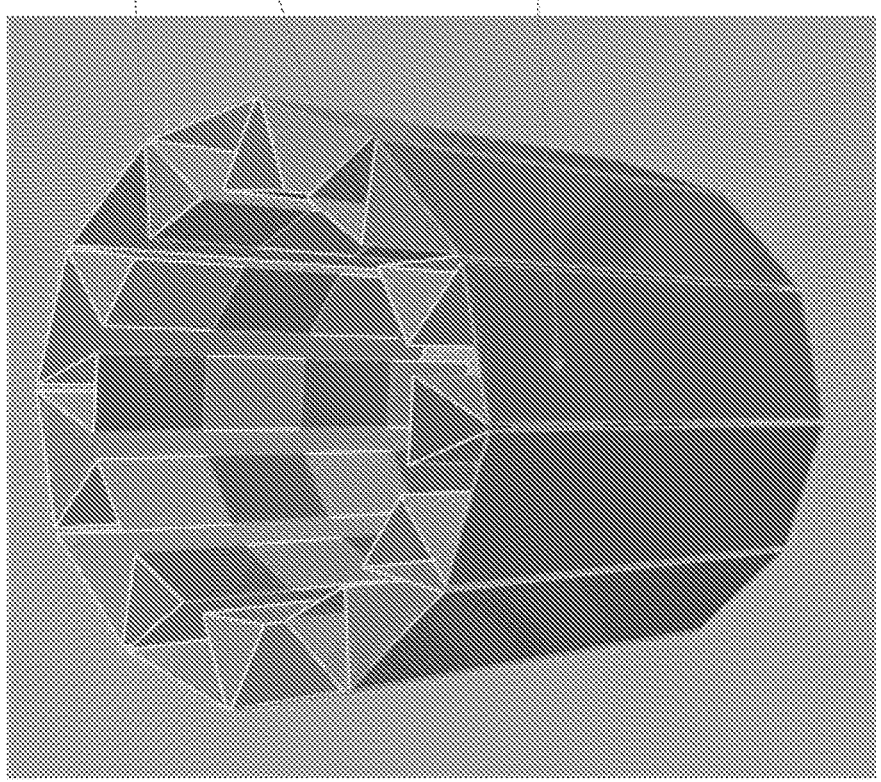

FIG. 1A illustrates one embodiment of a stretchable sensor design of the present invention. FIG. 1B illustrates a top view of the sensor in FIG. 1. The stretchable sensor design of this embodiment has 24 capacitance plates (1). On the outside of the sensor circumferentially (2) there are shielding ground plates. Between the inner layer of capacitance plates and the outer layer of ground plates, there exists an intermediate layer (3) that connects the two. This is the layer that houses the geometry sensing plates (4). Geometry sensing can be capacitance or other sensors integrated in this region.

The intermediate layer can be configured in any length to allow the sensor to accommodate a larger range of stretch. The longer the intermediate layer is between the inner layer and the outer layer, the greater the sensor can stretch. More plates can be incorporated using the concepts discussed herein to form virtually any number of sensor configurations. The plates themselves can be in any configuration or shape. In the preferred embodiment, the sensor substrate is created from a flexible material, such as nylon. As each of the three layers of the sensor while integrated can flex in one dimension, the sensor as a whole can stretch in two dimensions. (See FIG. 11 showing the changes in two dimensions indicated by the arrows).

The sensor substrate can also be created from a stretchable material, such as silicone or polyurethane, allowing the sensor to stretch in three dimensions. The substrate can be manufactured in a variety of ways, including extruded such as in 3D printing, injection molded, thermoformed, among other ways. The substrate can also be fashioned by traditional printed circuit board printing with the plates built in and formed into shape. In the preferred embodiment, the capacitive plates (1) are patterned in a staggered fashion to reduce inter-plate noise. The plates themselves are made of a conductive material such as copper (metals), conductive liquid, conductive ink, conductive spray, or even conductive filament in the setting of 3D printing. Low profile connectors are preferably used for directly interfacing each conductive plate with coaxial cables for connecting with a data acquisition system for collection sensor readings.

Figure 2B:
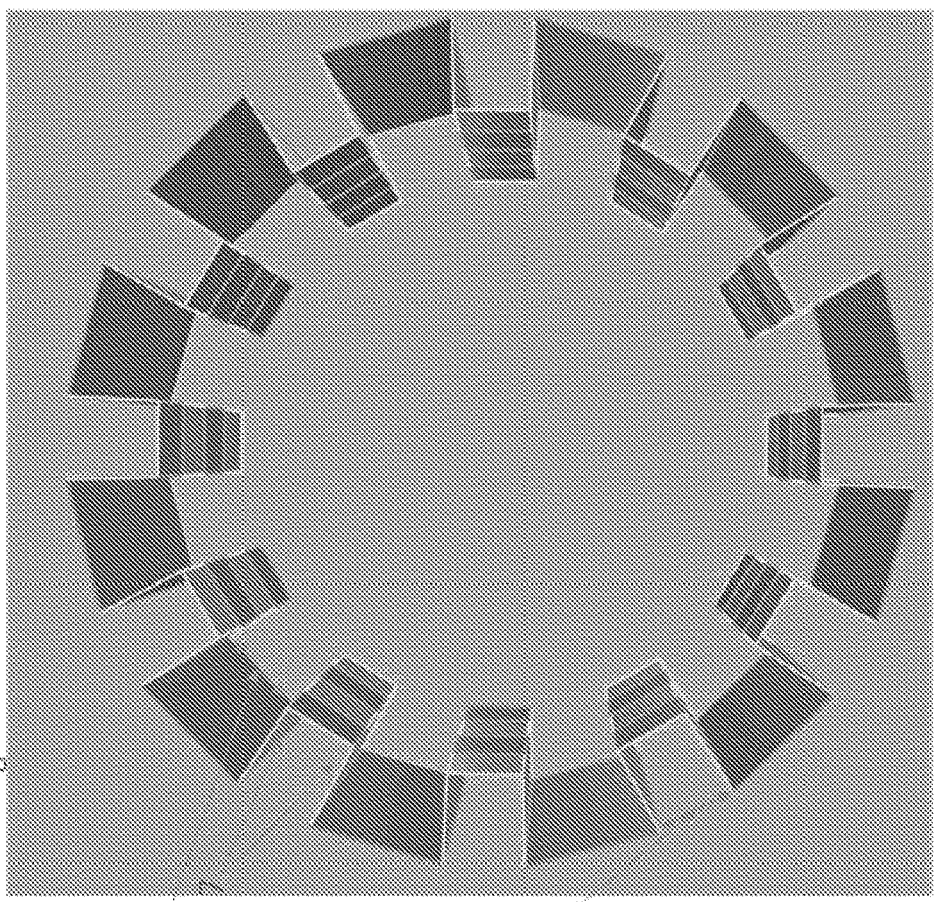
Figure 2A:
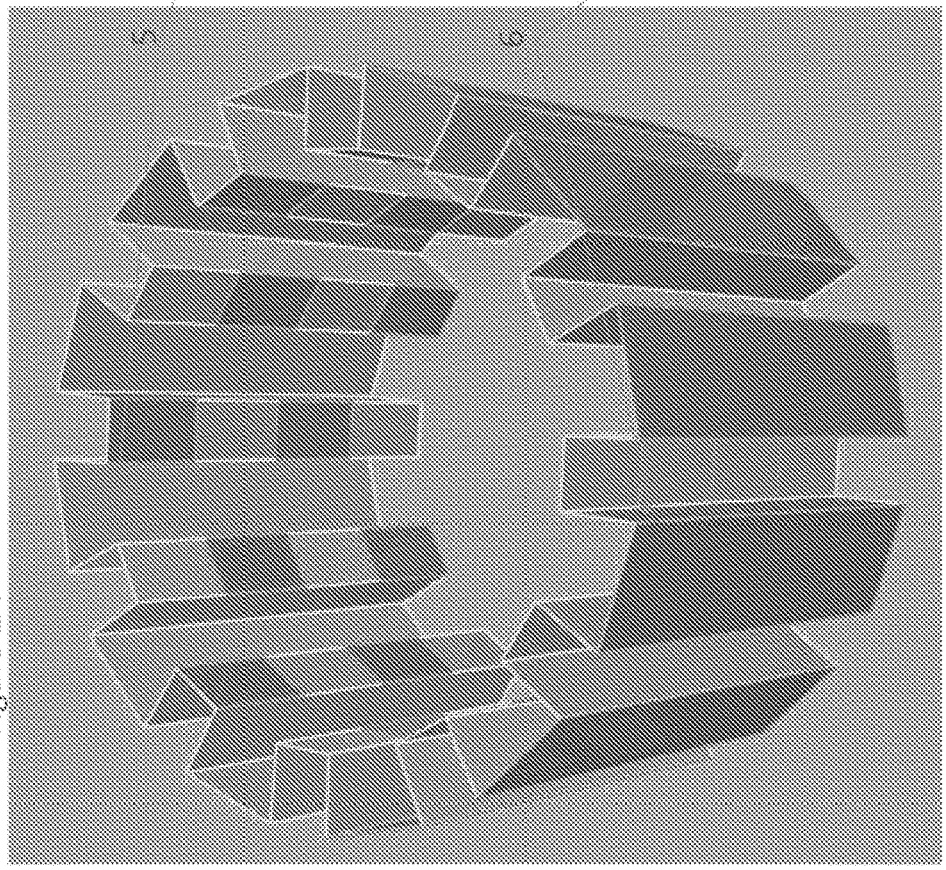

FIG. 2A illustrates the sensor in FIG. 1 in a stretched embodiment. FIG. 2B illustrates a top view of the sensor of FIG. 2. In the preferred embodiment, the sensor substrate is made of a flexible material. The design of the sensor orients this flexible material in two dimensions, allowing the sensor to stretch without stretching the substrate itself. This allows the conductive plates to maintain their continuity and integrity without requiring the plates themselves to expand. In a different embodiment of this stretchable sensor, the substrate can be made of an inherently stretchable material, allowing the sensor to stretch in all dimensions. This requires the conductive components of the sensor (capacitive plates, shielding ground plates, and geometry sensing plates) to be designed to allow stretching of the plates themselves.

In the preferred embodiment, when the sensor is stretched the distance between the conductive plates of the sensor changes (5) (6) and (7). The geometry sensing plates can recognize any change in the distance between them and the data acquisition can calculate the overall geometry of the sensor. Any number of geometry sensing plates can be used to increase the spatial resolution of the geometry calculations.

When the sensor expands the distance between the geometry sensing plates increases. The increase in distance will result in decrease in capacitance between those inner surfaces. Thus, from measuring the capacitance between those inner plates or surfaces, the system can determine how much the sensor expanded or compressed, and thus the shape and volume of the new geometry. The geometry sensor plates are preferably capacitance plates and can use the same measuring capacitance circuit as the sensor plates of the inner portion of the substrate. The geometry sensor plates can use the same acquisition data system simultaneously with the capacitance plates of the sensing domain or they can utilize an independent measuring circuit.

Figure 3A:
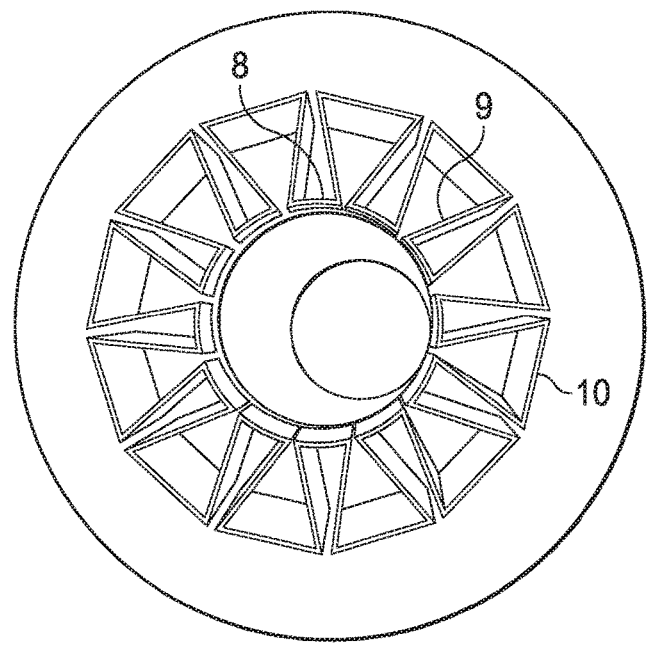
Figure 3B:
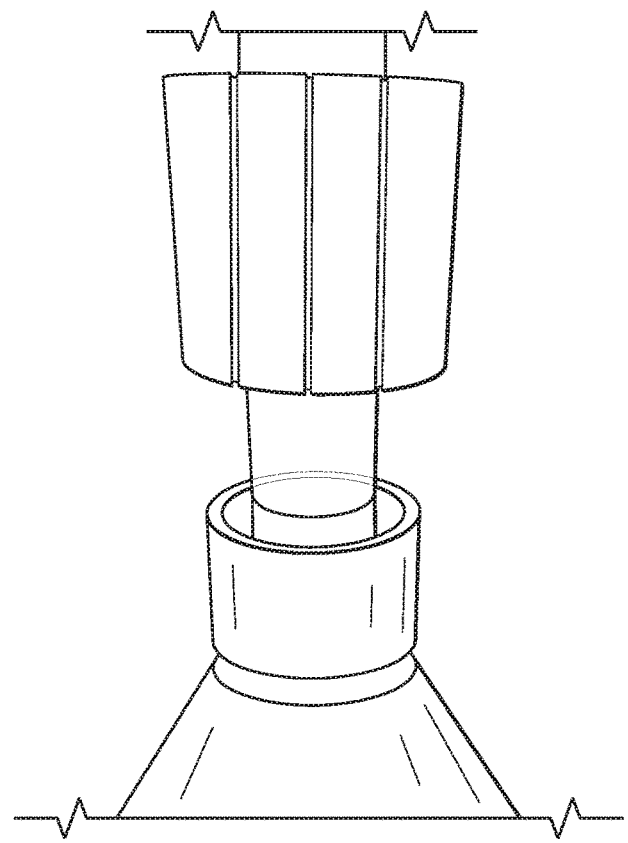
Figure 4A:
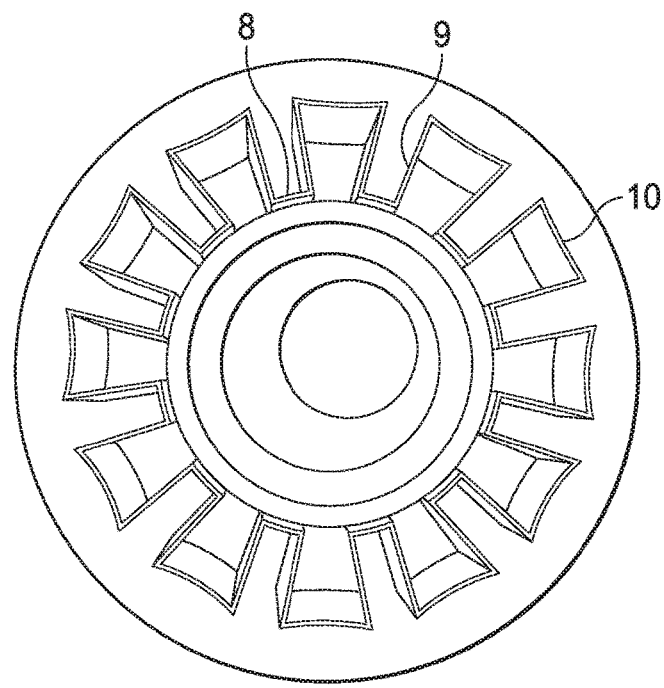
Figure 4B:
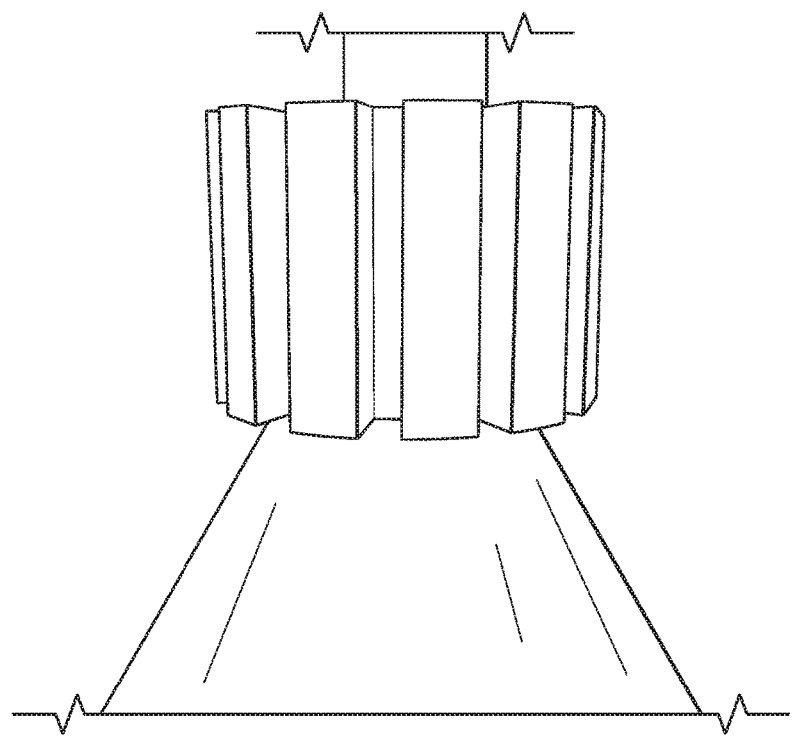
Figure 5A:
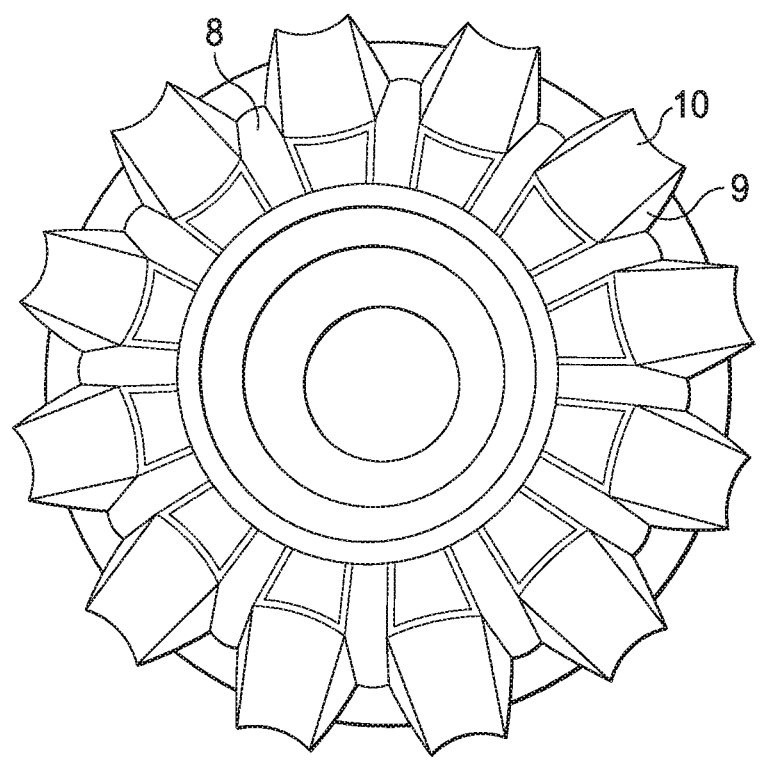
Figure 5B:
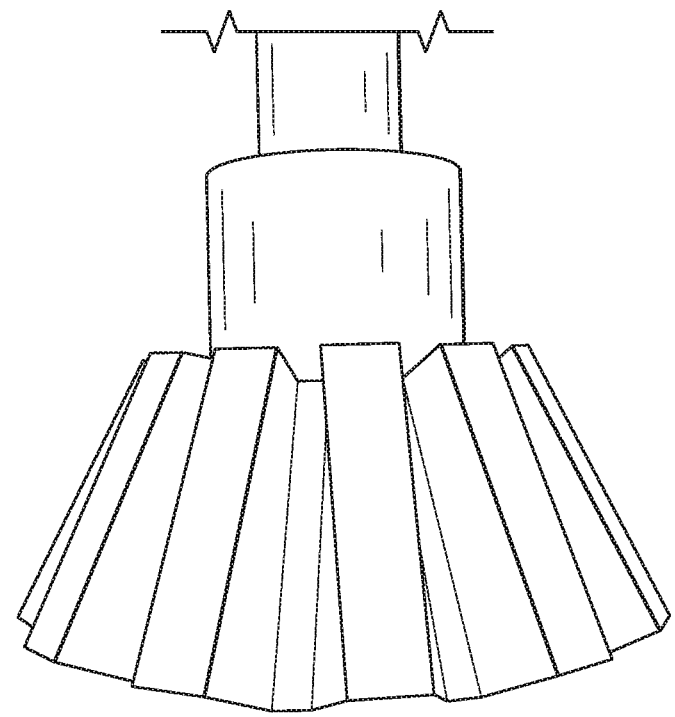

FIG. 3A illustrates a top view of one embodiment of a stretchable sensor in an example configuration. FIG. 3B illustrates the side view of the sensor of FIG. 3A. FIG. 4A illustrates a top view of the stretchable sensor of FIG. 3A in another example configuration. FIG. 4B illustrates the side view of the sensor of FIG. 4A. FIG. 5A illustrates a top view of the stretchable sensor of FIG. 3A in another example configuration. FIG. 5B illustrates the side view of the sensor of FIG. 5A.

In FIGS. 3A and 3B, the stretchable sensor is situated around the outflow pipe with a diameter of 2.5". In FIGS. 4A and 4B, the same sensor is stretched around the section of the model tract with a diameter of 4.5". In FIGS. 5A and 5B, the same sensor is stretched around the funneled portion of the model tract with a major diameter of 9" and a minor diameter of 4.5". The inner layer of capacitance plates in each of the three configurations are labelled with (8). The intermediate layer of geometry sensing plates in each of the three configurations are labelled (9). The outer layer of shielding ground plates in each of the three configurations are labelled (10).

FIG. 6A illustrates the top view of the sensor in FIG. 3A configured around a complex shape. FIG. 6B illustrates FIG. 6A from the side view.

FIG. 7 illustrates a side view of one embodiment of a stretchable sensor with 36 channels and minimal intermediate layer length to only allow for minute variations in the outside diameter of the pipe.

FIG. 8 illustrates one embodiment of the low profile connectors that are used to connect the capacitive, ground, and geometry-sensing plates of the stretchable sensor to the data acquisition via coaxial cables. The low profile connectors (20) are preferably used to directly connect the conductive plates of the sensor (capacitance plates, geometry sensing plates, and shielding ground plates) to the data acquisition box via a coaxial cable. This embodiment uses rivets (11) to connect the low profile connectors directly to the conductive plates. A black protective coating (12) protects all the conductive plates from abrasions and electrical shorting.

FIG. 9 illustrates one arrangement of inner sensor plate connections. The plate connections are applied on the inner layer of elastic substrate for forming a stretchable ECVT sensor. Conductive spray, liquid, or ink is applied to for forming conductive elements of integrative sensor layers. Elastic substrate can also be soaked in conductive liquid to form conductive parts of any layer in an integrative sensor. This concept can also be applied to the application of the signal traces.

FIG. 10A illustrates one example of conventional shaped capacitance plates. FIG. 10B illustrates one example of convex shaped capacitance plates. These plates assist in smoothing the sensor sensitivity in the imaging domain.

Further details regarding the theory and application of ECVT, sensor design, image reconstruction, and deployment of an ECVT system are found in the U.S. Patent Application Publication US 2010/0097374 (application Ser. No. 11/909, 548), the relevant disclosures of which are included by reference thereto as if fully set forth herein.

As depicted in FIGS. 1A and 1B of the U.S. Patent Application Publication US 2010/0097374 referenced herein, an array of electrodes (e.g., capacitance plates) are arranged to form a capacitance sensor. In one application, this sensor may be placed around a pipe or vent to detect movement within the receptacle to provide imaging data. In a conventional ECVT system, the sensor is made up of capacitance plates where the capacitance is measure between a selected pair of plates. The principle of the basic measuring circuit involves connecting one plate (source electrode or sending electrode) of the sensor to a voltage (e.g., Vi) and another plate (detecting electrode or receiving electrode) to a capacitance measurement circuit.

In one embodiment, the ECVT plates (i.e., electrodes) are comprised of an array of smaller capacitance segments that may be individually addressed. The shape of the capacitance segments can be made up of various shapes where each plate can be activated with the same or different voltages, frequencies, or phase shifts. Segments of each electrode are preferably connected together in parallel, with voltage control applied independently to each segment. Segments of interest chosen to form sender or receiver plates can be activated by electronic switches that open or close to connect a particular segment in parallel with others chosen in same plate. For example, each segment may be activated with different amplitudes, phase shifts, or frequency to provide the desired sensitivity matrix distribution. In one embodiment, the array of selected capacitance segments can form many pairs of capacitance electrodes or plates without reducing overall plate size. The capacitance segments can also be joined in different configurations to provide different designs.

In one embodiment of the invention as depicted in FIG. 11, the stretchable sensor apparatus is comprised of a substrate comprising: a plurality of inner portions (22) arranged in a circular arrangement, each inner portion having a first (24) and second (26) side, a plurality of outer portions (28) arranged in a circular arrangement, each outer portion having a first (30) and second (32) side, a plurality of intermediate portions (34), each intermediate portion connecting a side of one of the outer portions with a side of one of the inner portions and wherein the substrate is adapted to be stretched around objects of various diameters and shapes; a plurality of capacitance plates, each of the capacitance plates attached to one of the plurality of inner portions; a plurality of shielding ground plates, each of the shielding ground plates attached to one of the plurality of outer portions; a plurality of geometry sensing plates, each of the geometry sensing plates attached to one of the plurality of intermediate portions. The plurality of geometry sensing plates are adapted to detect signals for determining the shape of the volume the sensor is placed around. The ends of the intermediate portions and inner portions form triangle shapes (36) when then sensor is in the closed, non-stretched position.

In the embodiment shown, the capacitance plates are arranged in a staggered arrangement around the plurality of inner portions of the substrate. As illustrated in FIG. 11, the inner and outer portions of the substrate are arranged in a circular arrangement when the substrate is in a closed, non-stretched state.

In the embodiment shown in FIG. 11, the geometry sensing plates are capacitance plates adapted to sense the capacitance between the capacitance plates. The sensor is adapted to sense capacitance between the geometry sensing plates for determining the amount of compression or expansion of the sensor. In other words, as the length of the distance between the capacitance plates increases the capacitance decreases. This change in capacitance can be used to determine the distance between the plates and the geometry of the objection the sensor is placed around.

In an AECVT embodiment, the plurality of capacitance plates are comprised of: a first electrode, having a plurality of capacitance plate segments that are addressable with the voltage source; a second electrode, having a plurality of capacitance plate segments, the capacitance plate segments of the second electrode adapted to be connected electrically to a measurement circuit; and where the capacitance plate segments of the first electrode form capacitance pairs with at least one of the capacitance plate segments of the second electrode when activated.

In this embodiment the system is adapted to collect capacitance data by: defining a capacitor by using a capacitance plate segment on the first electrode as a source electrode, using a capacitance plate segment on the second electrode as a detecting electrode; charging and discharging the defined capacitor by directing a predetermined voltage to the source electrode from the voltage source; and detecting a capacitance of the defined capacitor by detecting a current induced in the detecting electrode.

The stretchable sensor of the present invention can be incorporated into a system for generating a three-dimensional tomograph of a vessel interior or other object. In one embodiment, the system is comprised of: a stretchable sensor apparatus adapted for placement around the vessel or the object, and where the stretchable sensor device is adapted to provide electric field distribution and sensor sensitivity in three geometric dimensions; data acquisition electronics in communication with the stretchable sensor apparatus for receiving input data from the stretchable sensor apparatus; and a processing system in communication with the data acquisition electronics, the processing system programmed with instructions for executing on the processing system to: 1) reconstruct a three-dimensional volume-image from the input data collected by the data acquisition electronics; and 2) reconstruct an image of the geometry of a volume it is placed around.

While certain embodiments of the present invention are described in detail above, the scope of the invention is not to be considered limited by such disclosure, and modifications are possible without departing from the spirit of the invention as evidenced by the following claims:

What is claimed is:

1. A stretchable sensor apparatus comprising:
   a substrate comprising: a plurality of first portions arranged in a circular arrangement, each first portion having a first and second side, a plurality of second portions arranged in a circular arrangement, each second portion having a first and second side, and wherein the substrate is adapted to be stretched around objects of various diameters and shapes;
   a plurality of capacitance plates, each of the capacitance plates attached to one of the plurality of first portions;
   a plurality of geometry sensing plates attached to the sensor apparatus; and
   wherein the plurality of geometry sensing plates are adapted to detect signals for determining a volume image of a volume the sensor apparatus is placed around.

2. The apparatus according to claim 1, wherein the substrate is comprised of stretchable material and wherein the substrate is further comprised of a plurality of intermediate portions, each intermediate portion connecting a side of one of the second portions with a side of one of the first portions;
   wherein the apparatus is further comprised of a plurality of shielding ground plates, each of the shielding ground plates attached to one of the plurality of second portions; and
   wherein each of the geometry sensing plates are attached to one of the plurality of intermediate portions.

3. The apparatus according to claim 2, wherein the length of the intermediate portions can be increased to increase the amount of stretch of the apparatus.

4. The apparatus according to claim 2, further comprising a plurality of low profile connectors for connecting the plurality capacitance, ground, and geometry sensing plates to a data acquisition system.

5. The apparatus according to claim 1, wherein the capacitance plates are arranged in a staggered arrangement around the plurality of first portions of the substrate.

6. The apparatus according to claim 1, wherein the first and second portions of the substrate are arranged in a circular arrangement when the substrate is in a closed, non-stretched state.

7. The apparatus according to claim 1, wherein the substrate is applied with conductive material for forming conductive layers.

8. The apparatus according to claim 1, wherein the each of the plurality of capacitance plates are in a convex plate shape to provide more homogeneous sensor sensitivity.

9. The apparatus according to claim 1, wherein the geometry sensing plates are capacitance plates and wherein the sensing plates is adapted to sense the capacitance between the capacitance plates.

10. The apparatus according to claim 9, wherein the sensor apparatus is adapted to sense capacitance between the geometry sensing plates for determining the amount of compression or expansion of the sensor apparatus.

11. The apparatus according to claim 1, wherein the plurality of capacitance plates are comprised of: a first electrode, having a plurality of capacitance plate segments that are addressable with a voltage source; a second electrode, having a plurality of capacitance plate segments, the capacitance plate segments of the second electrode adapted to be connected electrically to a measurement circuit; and wherein the capacitance plate segments of the first electrode form capacitance pairs with at least one of the capacitance plate segments of the second electrode when activated;

and wherein the apparatus is adapted to collect capacitance data by:
defining a capacitor by using a capacitance plate segment on the first electrode as a source electrode, using a capacitance plate segment on the second electrode as a detecting electrode,
charging and discharging the defined capacitor by directing a predetermined voltage to the source electrode from the voltage source;
detecting a capacitance of the defined capacitor by detecting a current induced in the detecting electrode.

12. A stretchable sensor apparatus comprising:
a substrate comprising: a plurality of first portions, each first portion having a first and second side, a plurality of second portions, each second portion having a first and second side, and wherein the substrate is adapted to be stretched around objects of various diameters and shapes;
a plurality of capacitance plates, each of the capacitance plates attached to one of the plurality of first portions;
a plurality of geometry sensing plates attached to the sensor apparatus and wherein the plurality of geometry sensing plates are adapted to detect signals for determining a volume image of a volume the sensor apparatus is placed around.

13. The apparatus according to claim 12, wherein the substrate is comprised of stretchable material, the substrate further comprising a plurality of intermediate portions, each intermediate portion connecting a side of one of the second portions with a side of one of the first portions and wherein each of the geometry sensing plates are attached to one of the plurality of intermediate portions.

14. The apparatus according to claim 13, wherein the ends of the intermediate portions and first portions form triangle shapes when the sensor apparatus is in the closed, non-stretched position.

15. The apparatus according to claim 12, wherein the plurality of capacitance plates are comprised of: a first electrode, having a plurality of capacitance plate segments that are addressable with a voltage source; a second electrode, having a plurality of capacitance plate segments, the capacitance plate segments of the second electrode adapted to be connected electrically to a measurement circuit; and wherein the capacitance plate segments of the first electrode form capacitance pairs with at least one of the capacitance plate segments of the second electrode when activated;
and wherein the apparatus is adapted to collect capacitance data by:
defining a capacitor by using a capacitance plate segment on the first electrode as a source electrode, using a capacitance plate segment on the second electrode as a detecting electrode,
charging and discharging the defined capacitor by directing a predetermined voltage to the source electrode from the voltage source;
detecting a capacitance of the defined capacitor by detecting a current induced in the detecting electrode.

16. The apparatus according to claim 12, wherein the sensor apparatus is adapted to sense capacitance between the geometry sensing plates for determining the amount of compression or expansion of the sensor apparatus.

17. The apparatus according to claim 16, wherein the geometry sensing plates are capacitance plates.

18. A system for generating a three-dimensional tomograph of a vessel interior or other object, the system comprising:
a stretchable sensor apparatus according to claim 12 for placement around the vessel or the object, wherein the stretchable sensor apparatus is adapted to provide electric field distribution and sensor sensitivity in three geometric dimensions;
data acquisition electronics in communication with the stretchable sensor apparatus for receiving input data from the stretchable sensor apparatus;
a processing system in communication with the data acquisition electronics, the processing system programmed with instructions for executing on the processing system to: 1) reconstruct a three-dimensional volume-image from the input data collected by the data acquisition electronics; and 2) reconstruct an image of the geometry of a volume it is placed around.

19. A system according to claim 18, wherein the processing system is programmed to calculate capacitance data from the input data received by the data acquisition electronics.

* * * * *